(12) United States Patent
Wang et al.

(10) Patent No.: US 12,226,181 B2
(45) Date of Patent: Feb. 18, 2025

(54) ABSORBENT COMPOSITE COMPRISING A HYDROENTANGLED NONWOVEN

(71) Applicant: AVINTIV Specialty Materials Inc., Charlotte, NC (US)

(72) Inventors: Lei Wang, Mooresville, NC (US); Nyle Bishop, Mooresville, NC (US); Ralph A. Moody, III, Mooresville, NC (US); Jerry Snider, Mooresville, NC (US); Pierre Grondin, Mooresville, NC (US)

(73) Assignee: AVINTIV SPECIALTY MATERIALS INC., Charlotte, NC (US)

( * ) Notice: Subject to any disclaimer, the term of this patent is extended or adjusted under 35 U.S.C. 154(b) by 1211 days.

(21) Appl. No.: 15/000,750

(22) Filed: Jan. 19, 2016

(65) Prior Publication Data

US 2016/0206393 A1    Jul. 21, 2016

Related U.S. Application Data

(60) Provisional application No. 62/104,120, filed on Jan. 16, 2015.

(51) Int. Cl.
| | |
|---|---|
| *A61B 46/00* | (2016.01) |
| *A61F 13/01* | (2024.01) |
| *A61F 13/15* | (2006.01) |
| *A61F 13/53* | (2006.01) |
| *A61F 13/84* | (2006.01) |
| *B32B 3/30* | (2006.01) |
| *B32B 5/02* | (2006.01) |
| *B32B 5/06* | (2006.01) |
| *B32B 5/08* | (2006.01) |
| *B32B 5/26* | (2006.01) |
| *B32B 27/12* | (2006.01) |

(Continued)

(52) U.S. Cl.
CPC ........ *A61B 46/40* (2016.02); *A61F 13/01029* (2024.01); *A61F 13/15203* (2013.01); *A61F 13/15804* (2013.01); *A61F 13/53* (2013.01); *A61F 13/8405* (2013.01); *B32B 3/30* (2013.01); *B32B 5/022* (2013.01); *B32B 5/06* (2013.01); *B32B 5/08* (2013.01); *B32B 5/26* (2013.01); *B32B 27/12* (2013.01); *B32B 27/306* (2013.01); *B32B 27/308* (2013.01); *B32B 27/32* (2013.01); *B32B 27/40* (2013.01); *D04H 1/492* (2013.01); *D04H 1/498* (2013.01); *D04H 3/16* (2013.01); *D04H 5/03* (2013.01); *A61F 2013/15463* (2013.01); *B32B 2260/021* (2013.01); *B32B 2260/046* (2013.01); *B32B 2262/0253* (2013.01); *B32B 2262/0261* (2013.01); *B32B 2262/0276* (2013.01); *B32B 2262/062* (2013.01); *B32B 2262/12* (2013.01); *B32B 2274/00* (2013.01); *B32B 2307/4023* (2013.01); *B32B 2307/7145* (2013.01); *B32B 2307/726* (2013.01); *B32B 2307/7265* (2013.01); *B32B 2307/728* (2013.01); *B32B 2307/75* (2013.01); *B32B 2535/00* (2013.01); *B32B 2556/00* (2013.01)

(58) Field of Classification Search
CPC ............... A61B 46/40; A61F 13/15203; A61F 13/15804; A61F 13/53; A61F 13/8405; A61F 2013/15463; A61F 13/00029; B32B 2260/021; B32B 2260/046; B32B 2262/0253; B32B 2262/0261; B32B 2262/0276; B32B 2262/062; B32B 2262/12; B32B 2274/00; B32B 2307/4023; B32B 2307/7145; B32B 2307/726; B32B 2307/7265; B32B 2307/728; B32B 2307/75; B32B 2535/00; B32B 2556/00; B32B 27/12; B32B 27/306; B32B 27/308; B32B 27/32; B32B 27/40; B32B 3/30; B32B 5/022; B32B 5/06; B32B 5/08; B32B 5/26; D04H 1/492; D04H 1/498; D04H 3/16; D04H 5/03

See application file for complete search history.

(56) References Cited

U.S. PATENT DOCUMENTS

| | | | | |
|---|---|---|---|---|
| 4,100,324 | A * | 7/1978 | Anderson | C11D 17/049 156/167 |
| 5,284,703 | A * | 2/1994 | Everhart | A61F 13/537 442/401 |

(Continued)

FOREIGN PATENT DOCUMENTS

WO    2007096470 A1    8/2007

OTHER PUBLICATIONS

Parikh et al.; J. Eng. Fibers and Fabrics; vol. 2, Iss. 3; pp. 40-49; published 2007.*

(Continued)

*Primary Examiner* — Jeffrey T. Palenik
(74) *Attorney, Agent, or Firm* — BURR & FORMAN LLP

(57) ABSTRACT

Absorbent composites suitable for a wide variety of uses (e.g., sorbent drapes, sorbent patches around a fenestration area, tray liners for surgical tools, incontinence pads and liners, other liners, etc.) are provided. The composite includes an absorbent nonwoven. The absorbent nonwoven may comprise a hydroentangled spunbond web. The composite also may comprise a liquid-impermeable film. One or more absorbent nonwovens of a composite may additionally comprise a three-dimensional pattern, for example, a three-dimensional pattern that has been imaged using hydroentanglement. Optionally, any one or more layers of the composites may comprise an antimicrobial additive.

13 Claims, 4 Drawing Sheets

(51) Int. Cl.
    *B32B 27/30*     (2006.01)
    *B32B 27/32*     (2006.01)
    *B32B 27/40*     (2006.01)
    *D04H 1/492*     (2012.01)
    *D04H 1/498*     (2012.01)
    *D04H 3/16*     (2006.01)
    *D04H 5/03*     (2012.01)

(56) References Cited

U.S. PATENT DOCUMENTS

| | | | |
|---|---|---|---|
| 5,901,706 | A | 5/1999 | Griesbach et al. |
| 6,314,627 | B1 | 11/2001 | Ngai |
| 6,735,833 | B2 | 5/2004 | Putnam et al. |
| 6,903,034 | B1 | 6/2005 | Putnam et al. |
| 7,091,140 | B1 | 8/2006 | Ferencz et al. |
| 7,230,043 | B2* | 6/2007 | Klun ............ C08K 5/435 524/243 |
| 7,406,755 | B2 | 8/2008 | Putnam et al. |
| 7,455,800 | B2 | 11/2008 | Ferencz et al. |
| 2002/0168910 | A1 | 11/2002 | Vuillaume et al. |
| 2006/0052495 | A1* | 3/2006 | Klun ............ C08K 5/435 524/502 |
| 2006/0093788 | A1* | 5/2006 | Behm ............ A47J 47/005 428/137 |
| 2006/0160453 | A1 | 7/2006 | Suh |
| 2006/0185134 | A1 | 8/2006 | Carter et al. |
| 2008/0028560 | A1* | 2/2008 | Policicchio ...... C11D 1/662 15/229.3 |

OTHER PUBLICATIONS

International Search Report and Written Opinion of corresponding application No. PCT/US2016/013893, mailed May 3, 2016, all enclosed pages cited.

Second Written Opinion of corresponding International Application No. PCT/US2016/013893 mailed Dec. 14, 2016, all enclosed pages cited.

Third Written Opinion of corresponding International Application No. PCT/US2016/013893 mailed Feb. 28, 2017, all enclosed pages cited.

* cited by examiner

ABSORBENT COMPOSITE COMPRISING A HYDROENTANGLED NONWOVEN

CROSS-REFERENCE TO RELATED APPLICATIONS

This patent application claims the priority benefit of U.S. Provisional Application No. 62/104,120 filed on Jan. 16, 2015, the contents of which are incorporated herein by reference.

TECHNICAL FIELD

The presently-disclosed invention relates generally to absorbent composites having various commercial applications.

BACKGROUND

Absorbent articles are commonly used to absorb and contain fluids, thereby preventing contamination of surfaces and people. Absorbent articles are frequently used in applications related to surgical procedures (e.g., sorbent drapes, sorbent patches around a fenestration area, tray liners for surgical tools, etc.). Sorbent drapes, for example, may be part of the infection control system used during surgical procedures in order to protect the patients as well as medical staff. A desirable property for sorbent surgical drapes is impermeability to the fluids generated during surgery in order to avoid contamination. Another desirable property for sorbent surgical drapes is absorbency to contain fluids, reduce the labor related to decontamination of the operating room, and reduce the risk of contamination to the medical personnel.

One approach to provide absorbency to surgical drapes has been to provide limited areas or patches that are absorbent in the vicinity of the opening in the surgical drape. This type of drape is often referred to as a fenestration drape. Another approach has been to use an absorbent nonwoven that covers all or at least a large section of the drape. This type of drape is often referred to as a sorbent drape.

Absorbent drapes have conventionally been made by forming a composite comprising a film and an absorbent nonwoven. Typically, these drapes consist of a laminate with a film in the middle and a nonwoven glued to it on each side such that the nonwoven facing the outside during the surgical intervention is absorbent.

Spunbond has conventionally been the preferred nonwoven for such applications because of its low cost, its ability to be rendered absorbent by incorporation of or a topical treatment with a surfactant, its low tendency of shedding particulates (i.e., low linting), its good tensile strength, and its good abrasion resistance. Nonwovens comprising wood pulp such as airlaid or wetlaid nonwovens have also been used but they typically do not perform as well with respect to linting and abrasion resistance.

In such applications, the barrier to liquid penetration is commonly a plastic film adhesively bonded to the nonwovens. Another option that is more cost effective is to extrusion coat the plastic film directly on the nonwoven; however, this approach typically reduces the absorption capacity of the absorbent nonwoven when compared to adhesive lamination methods.

Therefore, there at least remains a need in the art for a product that provides a cost-effective absorbent nonwoven based, at least in part, on a spunbond web with a film extrusion coated on the absorbent nonwoven, in which the composite exhibits one or more of a superior absorbency, an acceptable abrasion resistance, and low linting.

SUMMARY OF INVENTION

One or more embodiments of the invention may address one or more of the aforementioned problems. Certain embodiments, according to the invention, provide absorbent composites suitable for a wide variety of uses (e.g., sorbent drapes, sorbent patches around a fenestration area, tray liners for surgical tools, incontinence pads and liners, other liners, etc.). In one aspect, the composite includes an absorbent nonwoven. The absorbent nonwoven may comprise a hydroentangled spunbond web. The composite also may comprise a liquid-impermeable film.

In an embodiment of the invention, the liquid-impermeable film may be embedded, at least embedded in part, into the absorbent nonwoven. For example, the liquid-impermeable film may extend into the absorbent nonwoven by at least about 5 percent of the thickness of the absorbent material.

The liquid-impermeable film may be disposed on the absorbent nonwoven by any technique known in the art. According to an embodiment of the invention, the liquid-impermeable film may be extrusion coated on the absorbent nonwoven.

The hydroentangled spunbond web of the absorbent nonwoven may comprise one or more spunbond webs, according to an embodiment of the invention. In certain embodiments of the invention, the absorbent nonwoven may further comprise one or more meltblown layers. In certain embodiments of the invention, the absorbent nonwoven may further comprise at least one nanofiber layer or a layer having nanofibers according to one embodiment of the invention and microfibers according to another embodiment of the invention.

In an embodiment of the invention, the absorbent nonwoven comprises synthetic polymer filaments. For example, in an embodiment of the invention, the synthetic polymer filaments may comprise any of a polyolefin, a polyester, a polyamide, or any combination thereof. In another embodiment of the invention, the synthetic polymer filaments may comprise polyethylene, polypropylene, partially aromatic polyesters, fully aromatic polyesters, polyhexamethylene diadipamide, polycaprolactam, aromatic or partially aromatic polyamides, aliphatic polyamides, and combinations thereof. In yet another embodiment of the invention, the synthetic polymer filaments comprise any of polypropylene, partially aromatic polyesters, fully aromatic polyesters, or any combination thereof. In even yet another embodiment of the invention, the synthetic polymer filaments comprises one or more of partially aromatic polyesters and fully aromatic polyesters. The synthetic polymer filaments may comprise polyethylene terephthalate, according to an embodiment of the invention.

According to an embodiment of the invention, the synthetic polymer filaments may comprise a multicomponent fiber such as, for example, a bicomponent filament. The bicomponent filament may comprise a sheath and a core. According to an embodiment of the invention, the sheath may comprise a polyolefin such as, for example a polyethylene, a polypropylene, and any combination thereof. In an embodiment of the invention, the core may comprise a polyolefin, a polyester, and combinations thereof. According to certain embodiments of the invention, the sheath may comprise a polypropylene and a polyester, for example.

In certain embodiments of the invention, the synthetic polymer filaments may comprise a surfactant. In certain embodiments of the invention, the absorbent nonwoven comprises a topical surfactant. In an embodiment of the invention, the absorbent nonwoven may be hydrophilic.

In certain embodiment, the composite may further comprise a second nonwoven, such as a non-absorbent nonwoven. In certain example, the second nonwoven may comprise at least one spunbond layer, at least one meltblown layer, at least one nanofiber, layer, or any combinations thereof. In this regard, composites according to certain embodiments may comprise an absorbent nonwoven as disclosed herein, a liquid-impermeable film, and a second nonwoven, such as anon-absorbent nonwoven.

As referenced above, the composite according to certain embodiments may comprise a liquid-impermeable film, such as a breathable polymer film. In certain embodiments, the liquid-impermeable film may comprise at least one hygroscopic polymer, which may comprise, for example, at least one polyolefin polymer and combinations thereof. For example, the liquid-impermeable film may comprise at least one of polyethylene, ethylene-vinyl acetate, ethyl methyl acrylate, polypropylene, plastomer or elastomeric polyolefin, thermoplastic urethane, polyether block amide copolymer, copolyester thermoplastic elastomer, or any combinations thereof. The liquid-impermeable film may be extrusion coated onto the absorbent nonwoven or extrusion coated between the absorbent nonwoven and the second nonwoven (if the second nonwoven is present). In certain embodiments, an outer surface of the composite comprises the hydroentangled web.

In certain embodiments, the composite may include one or more additives, such as one or more antimicrobial agents or additives. For example, the composite according to certain embodiments, at least one of the absorbent nonwoven, the liquid-impermeable film, or both may comprise an antimicrobial agent or additive.

In another aspect, the composite includes an absorbent nonwoven comprising a hydroentangled composite. The hydroentangled composite may comprise a layer of cellulose fiber (e.g., one or more layers of cellulose fiber) positioned between two nonwoven webs. The composite may also comprise a liquid-impermeable film. In certain embodiments, one or both of the nonwoven webs may comprise one or more spunbond webs. In accordance with certain embodiments, one or both nonwoven webs may further comprise one or more meltblown layer and/or one or more nanofiber layers. In certain embodiments, the layer(s) of cellulose fiber may be air-laid or wet-laid. In certain embodiments, the layer(s) of cellulose fiber may comprise a tissue paper. The cellulose fiber layer(s) may, according to certain embodiments, comprise a layer(s) of wood pulp fiber.

As referenced above, the composite may comprise a liquid-impermeable film, such as a breathable polymer film. In certain embodiments, the liquid-impermeable film may comprise at least one hygroscopic polymer, such as at least one polyolefin polymer and combinations thereof. For example, the liquid-impermeable film, in accordance with certain embodiments, may comprise at least one of polyethylene, ethylene-vinyl acetate, ethyl methyl acrylate, polypropylene, plastomer or elastomeric polyolefin, thermoplastic urethane, polyether block amide copolymer, copolyester thermoplastic elastomer, or any combinations thereof. In accordance with certain embodiments, at least one of the two nonwoven webs, the liquid-impermeable film, and any combination thereof may comprise an antimicrobial agent or additive.

In another aspect, certain embodiments of the invention provide a process for forming a composite. The process may comprise hydroentangling a nonwoven material comprising at least one spunbond web to form an absorbent nonwoven and extrusion coating a liquid-impermeable film onto a surface of the absorbent nonwoven. The process may further comprise melt-spinning a polymer composition and forming the at least one spunbond web. In accordance with certain embodiments, the process may further comprise positioning a first side of the absorbent nonwoven directly or indirectly onto an image transfer device having a three-dimensional pattern and applying jets of fluid directly or indirectly to a second side of the absorbent nonwoven to impart a three-dimensional pattern onto the absorbent nonwoven.

In certain embodiments, the process may comprise forming the polymer composition. The polymer composition can comprise, for example, at least one of polyolefins, polyesters, polyamides, and combinations thereof. In certain embodiments, the polymer composition may comprise at least one of polyethylene, polypropylene, partially aromatic or fully aromatic polyesters, polyhexamethylene diadipamide, polycaprolactam, aromatic or partially aromatic polyamides, aliphatic polyamides, or any combinations thereof. In accordance with certain embodiments, the step of forming the polymer composition may comprise forming a first and a second polymer composition followed by melt-spinning the first and second polymer composition through a die for forming bicomponent fibers, wherein the bicomponent fibers have a sheath and a core. In certain embodiments, the sheath and/or core may comprise, for example, a polyolefin, polyester, and combinations thereof. The polymer composition (e.g., the first polymer composition) may comprise a surfactant.

As referenced above, the process may comprise extrusion coating the liquid-impermeable film onto a surface of the absorbent nonwoven. The liquid-impermeable film, for example, may comprise a breathable polymer film. In certain embodiments, the liquid-impermeable film may comprise at least one hygroscopic polymer (e.g., at least one polyolefin polymer and combinations thereof). The liquid-impermeable film, in accordance with certain embodiments, may comprise at least one of polyethylene, ethylene-vinyl acetate, ethyl methyl acrylate, polypropylene, plastomer or elastomeric polyolefin, thermoplastic urethane, polyether block amide copolymer, copolyester thermoplastic elastomer, or any combinations thereof.

In certain embodiments, the process may further comprise attaching a second nonwoven web (e.g., a non-absorbent nonwoven), wherein the liquid-impermeable film may be positioned between the absorbent nonwoven and the second nonwoven web. The second nonwoven, as discussed above, may comprise at least one spunbond layer, at least one meltblown layer, and/or at least one nanofiber layer.

In accordance with certain embodiments, the at least one spunbond web may comprise at least two spunbond webs. In certain embodiments, the process may further comprise depositing a layer (or layers) of cellulose fiber indirectly of directly between the at least two spunbond webs to provide a nonwoven material. The process may further comprise hydroentangling the nonwoven material to form the absorbent nonwoven. In certain embodiments, the step of depositing the layer of cellulose fiber between the at least two spunbond webs may comprise air laying the layer of cellulose fiber, wet laying the layer of cellulose fiber, or introducing a tissue paper. In certain embodiments, the layer of cellulose fiber may comprise a layer of wood pulp fiber.

In certain embodiments, the process may further comprise adding one or more additives (e.g., surfactant) into the polymer composition used for forming at least one of the webs of composite. Additionally or alternatively, one or more additives (e.g., surfactant) may be topically applied onto a surface of the absorbent nonwoven. In certain embodiments, the process may comprise forming and/or treating any of one or more of the at least one spunbond web, the liquid-impermeable film, or any combination thereof with an antimicrobial agent or additive.

BRIEF DESCRIPTION OF THE DRAWING(S)

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

DETAILED DESCRIPTION

Figure 1:
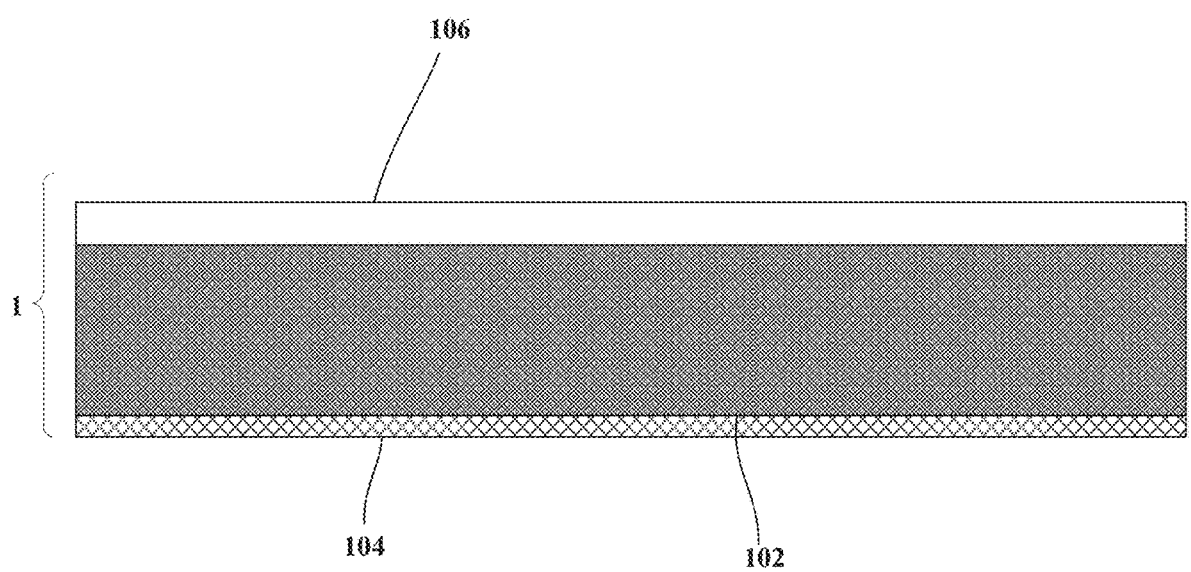
FIG. 1 illustrates a cross-sectional view of an absorbent composite according to an embodiment of the invention.

The invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

Any relative dimensions illustrated in the figures are given by way of example and are not intended to be limiting. As would be appreciated by a person having ordinary skill in the art, the relative dimensions can vary depending on any number of factors including, without limitation, the intended use and performance of the illustrated article.

The invention includes, according to certain embodiments, an absorbent nonwoven based, at least in part, on a spunbond web with a film extrusion coated on the absorbent nonwoven. Composites, according to certain embodiments of the invention, may exhibit one or more of a superior absorbency, an acceptable abrasion resistance, and low linting.

The term "substantial" may encompass the whole amount as specified, according to certain embodiments of the invention, or largely but not the whole amount specified according to other embodiments of the invention.

The terms "polymer" or "polymeric", as used interchangeably herein, may comprise homopolymers, copolymers, such as, for example, block, graft, random, and alternating copolymers, terpolymers, etc., and blends and modifications thereof. Furthermore, unless otherwise specifically limited, the term "polymer" or "polymeric" shall include all possible structural isomers; stereoisomers including, without limitation, geometric isomers, optical isomers or enantiomers; and/or any chiral molecular configuration of such polymer or polymeric material. These configurations include, but are not limited to, isotactic, syndiotactic, and atactic configurations of such polymer or polymeric material.

The term "breathable film", as used herein, may comprise any film that is selectively permeable to water vapor but substantially impermeable to liquid water. Breathable films may comprise, for example, polyethylene, ethylene-vinyl acetate, ethyl methyl acrylate, polypropylene, plastomer or elastomeric polyolefin (e.g., VISTAMAXX™ from ExxonMobil Chemical Company, VERSIFY™ and AFFINITY™ from The Dow Chemical Company), polyether block amide copolymer (e.g., PEBAX® from Arkema Group), polyester block amide copolymer, copolyester thermoplastic elastomer (e.g., ARNITEL® from DSM Engineering Plastics, HYTREL® from ET DuPont de Nemours and Company), thermoplastic urethane elastomer, and combinations thereof.

The terms "nonwoven" and "nonwoven web", as used herein, may comprise a web having a structure of individual fibers, filaments, and/or threads that are interlaid but not in an identifiable repeating manner as in a knitted or woven fabric. Nonwoven fabrics or webs, according to certain embodiments of the invention, may be formed by any process known in the art such as, for example, meltblowing processes, spunbonding processes, hydroentangling, airlaid, and bonded carded web processes.

The term "layer", as used herein, may comprise a generally recognizable combination of similar material types and/or functions existing in the X-Y plane.

The term "composite", as used herein, may comprise a structure comprising two or more layers, such as a film layer and a nonwoven layer. The two layers of a composite structure may be joined together such that a substantial portion of their common X-Y plane interface, according to certain embodiments of the invention.

The term "spunbond", as used herein, may comprise fibers which are formed by extruding molten thermoplastic material as filaments from a plurality of fine, usually circular, capillaries of a spinneret with the diameter of the extruded filaments then being rapidly reduced. According to an embodiment of the invention, spunbond fibers are generally not tacky when they are deposited onto a collecting surface and may be generally continuous. It is noted that the spunbond used in certain composites of the invention may include nonwovens described in the literature as SPINLACE®.

The term "meltblown", as used herein, may comprise fibers formed by extruding a molten thermoplastic material through a plurality of fine die capillaries as molten threads or filaments into high velocity, usually hot, gas (e.g. air) streams which attenuate the filaments of molten thermoplastic in to reduce their diameter, which may be to microfiber diameter, according to certain embodiments of the invention. According to an embodiment of the invention, the die capillaries may be circular. Thereafter, the meltblown fibers are carried by the high velocity gas stream and are deposited on a collecting surface to form a web of randomly disbursed meltblown fibers. Meltblown fibers are microfibers which may be continuous or discontinuous and are generally tacky when deposited onto a collecting surface.

The term "nanofiber", as used herein, may comprise fibers having diameters of less than about 1000 nanometers (i.e., less than about one micron). Without intending to be bound by theory, nanofiber webs may be desired in certain embodiments of the invention, for example, due to their high surface area and low pore size, among other characteristics. Methods of producing nanofibers include melt fibrillation. Melt fibrillation is a general class of fiber production in which one or more polymers are molten and extruded into many possible configurations (e.g., co-extrusion, homogeneous or bicomponent films or filaments) and then fibrillated or fiberized into filaments. Non-limiting examples of melt fibrillation methods comprise melt blowing, melt fiber bursting, and melt film fibrillation. Methods of producing nanofibers not from melts comprise film fibrillation, electrospinning, and solution spinning. Other methods of producing nanofibers include spinning a larger diameter bicomponent fiber in an islands-in-the-sea, segmented pie, or other configuration where the fiber is then further processed so that nanofibers result.

The term "hydroentangle", as used herein, may comprise a process for bonding a nonwoven fabric by using high pressure water jets to intermingle the fibers. Several rows of water jets are directed against the fiber web, which is supported by a movable fabric. Fiber entanglements are introduced by the combined effects of the water jets and the turbulent water created in the web, which intertwines neighboring fibers.

The term "cellulose fiber", as used herein, may comprise a variety of products comprising cellulose. Cellulose may refer to a natural carbohydrate polymer having the chemical formula $(C_5H_{10}O_5)_n$ and consisting of anhydro-glucose units joined by an oxygen linkage to form long molecular chains that are essentially linear. Natural sources of cellulose may comprise deciduous and coniferous trees (e.g., wood), cotton, flax, esparto grass, milkweed, straw, jute, hemp, and bagasse. The cellulose may have been processed by such treatments as, for example, thermal, chemical, and/or mechanical treatments to form cellulose fiber (e.g. wood pulp fiber).

I. Composite

In one aspect, the invention provides an absorbent composite suitable for a wide variety of end uses. In one aspect, the composite includes an absorbent nonwoven, which may comprise a hydroentangled spunbond web. The composite may also comprise a liquid-impermeable film. In certain embodiments, an outer surface of the composite may comprise the hydroentangled web.

In accordance with certain embodiments of the invention, the liquid-impermeable film may be at least partially embedded into the absorbent nonwoven. Further pursuant to this embodiment, for example, the liquid-impermeable film may extend into the absorbent nonwoven at least 5 percent of a thickness of the absorbent nonwoven. According to certain embodiments, the liquid-impermeable film may be extrusion coated on the absorbent nonwoven. In this regard, the extrusion coated liquid-impermeable film may at least partially flow into and impregnate the voids between fibers of the nonwoven adjacent the film such that the liquid-impermeable film is at least partially embedded in the nonwoven. As such, in certain embodiments the liquid-impermeable film may extend into the absorbent nonwoven at a percentage of the thickness of the absorbent nonwoven from at least about any of the following: 1, 2, 3, 5, and 10% and/or at most about 20, 18, 15, 12, 10, 9, 8, 7, 6, and 5% (e.g., about 5-10%, about 5-20%, etc.).

In accordance with certain embodiments of the invention, the liquid-impermeable film may comprise a breathable polymer film. In some embodiments, the liquid-impermeable film may comprise at least one hygroscopic polymer. In other embodiments, the liquid-impermeable film may comprise at least one polyolefin polymer and combinations thereof. In further embodiments, the liquid-impermeable film may comprise at least one of polyethylene, ethylene-vinyl acetate, ethyl methyl acrylate, polypropylene, plastomer or elastomeric polyolefin (e.g., VISTAMAXX™ from ExxonMobil Chemical Company, VERSIFY™ and AFFINITY™ from The Dow Chemical Company), thermoplastic urethane, polyether block amide copolymer (e.g., PEBAX® from Arkema Group), copolyester thermoplastic elastomer (e.g., ARNITEL® resin from DSM Engineering Plastics, HYTREL® from E.I. Dupont de Nemours and Company), and combinations thereof. According to certain embodiments, the film may comprise an extrusion coated film.

In accordance with certain embodiments of the invention, for example, the hydroentangled spunbond web may comprise a plurality of spunbond webs. In addition, for instance, the absorbent nonwoven may further comprise at least one meltblown layer. Alternatively or in addition, for instance, the absorbent nonwoven may comprise a nanofiber and/or further comprise at least one nanofiber layer. In accordance with certain embodiments, the absorbent nonwoven may comprise any combination of meltblown, spunbond, and nanofiber layers in a variety of configurations. Exemplary configurations include, but are not limited to, SMS, SMNS, SSMMS, SSMNS, etc., where S=spunbond layer, M=meltblown layer, and N=nanofiber layer. In certain embodiments, the absorbent nonwoven may also optionally include a film layer.

In accordance with certain embodiments of the invention, the absorbent nonwoven may comprise a three-dimensional pattern. Further pursuant to this embodiment, for example, imaging the absorbent nonwoven with a three-dimensional pattern may one or both of improve liquid absorption and reduce liquid run-off.

In accordance with certain embodiments of the invention, the absorbent nonwoven may comprise synthetic polymer filaments. Further pursuant to this embodiment, for example, the polymer filaments may comprise at least one of a polyolefin, a polyester, a polyamide, or any combination thereof. In some embodiments, for example, the polymer filaments may comprise at least one of polyethylene, polypropylene, partially aromatic or fully aromatic polyesters (e.g., polyethylene terephthalate), polyhexamethylene diadipamide, polycaprolactam, aromatic or partially aromatic polyamides, aliphatic polyamides, and combinations thereof. In other embodiments, for instance, the polymer filaments may comprise at least one of polypropylene, partially aromatic or fully aromatic polyesters (e.g., polyethylene terephthalate), and combinations thereof. In further embodiments, for example, the polymer filaments may comprise polypropylene. In other embodiments, for instance, the polymer filaments may comprise partially aromatic or fully aromatic polyesters (e.g., polyethylene terephthalate). In further embodiments, for example, the polymer filaments may comprise polyethylene terephthalate.

According to certain embodiments of the invention, the polymer filaments may comprise one or more multicomponent fibers. Further pursuant to this embodiment, the multicomponent fibers may comprise or, according to other embodiments, only include bicomponent fibers having a sheath and a core. Further pursuant to this embodiment, for example, the sheath may comprise a polyolefin. In some embodiments, for instance, the sheath may comprise at least one of a polyethylene or polypropylene. In further embodiments, for example, the sheath may comprise polyethylene. According to some embodiments, for instance, the core may comprise at least one of a polyolefin or polyester. In other embodiments, for example, the core may comprise at least one of polyethylene, polypropylene, polyester, and combinations thereof. In further embodiments, for instance, the core may comprise at least one of polypropylene or polyester.

According to certain embodiments of the invention, the absorbent nonwoven may be hydrophilic. Further pursuant to this embodiment, the polymer filaments may further comprise a surfactant. For instance, the polymeric melt used for forming the filaments may include a hydrophilic additive (e.g., hydrophilic surfactant that increases the wettability of the filaments), rendering the formed filaments hydrophilic. Further pursuant to these embodiments, a binder may be included with the hydrophilic additive. Alternatively or in addition, the absorbent nonwoven may comprise a topical surfactant to render the absorbent nonwoven hydrophilic. In some embodiments, the absorbent nonwoven may be treated with a topical surfactant after being imaged with a three-dimensional pattern. In certain embodiments, for instance, the inclusion of surfactant molecules either in the polymer filaments or as a topical treatment of the absorbent nonwoven may increase wettability of the absorbent nonwoven.

In accordance with certain embodiments of the invention, the composite may further comprise a second nonwoven. Further pursuant to this embodiment, for example, the second nonwoven may comprise a non-absorbent nonwoven. In some embodiments, for instance, the second nonwoven may comprise at least one spunbond layer. Alternatively or in addition, for example, the second nonwoven may comprise at least one meltblown layer. Alternatively or in addition, for instance, the second nonwoven may comprise at least one nanofiber layer.

According to certain embodiments of the invention, the liquid-impermeable film may be extrusion coated between the absorbent nonwoven and the second nonwoven. Further pursuant to this embodiment, the liquid-impermeable film may be at least partially embedded in both nonwovens. Even further pursuant to this embodiment, for example, the liquid-impermeable film may extend into the nonwovens at least 5 percent of their respective thicknesses. In this regard, the extrusion coated liquid-impermeable film may at least partially flow into and impregnate the voids between fibers of the nonwovens adjacent the film such that the liquid-impermeable film is at least partially embedded in the nonwovens. As such, in certain embodiments the liquid-impermeable film may extend into the nonwovens at a percentage of the thicknesses of the nonwovens from at least about any of the following: 1, 2, 3, 5, and 10% and/or at most about 20, 18, 15, 12, 10, 9, 8, 7, 6, and 5% (e.g., about 5-10%, about 5-20%, etc.). In certain embodiments, an outer surface of the composite may comprise a hydroentangled web.

In accordance with certain embodiments of the invention, the composite may comprise or consist only of two layers. Further pursuant to this embodiment, these two layers, for example, may comprise only an absorbent nonwoven and a liquid-impermeable film extrusion coated directly or indirectly on the absorbent nonwoven. In other embodiments, the composite may comprise or consist only of three layers. Further pursuant to this embodiment, these three layers, for example, may comprise only an absorbent nonwoven, a second nonwoven (e.g., non-absorbent spunbond), and a liquid-impermeable film extrusion coated directly or indirectly between the absorbent nonwoven and the second nonwoven.

In accordance with certain embodiments of the invention, for example, the composite may have a normalized absorbency from about 5 to about 20. In other embodiments, for instance, the composite may have a normalized absorbency from about 8 to about 18. In further embodiments, for example, the composite may have a normalized absorbency from about 10 to about 15. As such, in certain embodiments, the composite may have a normalized absorbency from at least about any of the following: 5, 8, and 10 and/or at most about 20, 18, and 15 (e.g., about 5-20, about 10-18, etc.). Composite Normalized Absorbency is an index developed by first measuring the weight of water absorbed by sq. meter of composite as per the Absorption Capacity test and dividing that number by the weight per sq. meter of the absorbent nonwoven layer used in the composite.

In accordance with certain embodiments of the invention, for instance, the composite may have a 1 mL Absorption Time of less than 10 seconds. In other embodiments, for example, the composite may have a 1 mL Absorption Time of less than 5 seconds. As such, in certain embodiments, the composite may have a 1 mL Absorption Time from at most about any of the following: 10, 9, 8, 7, 6, 5, and 1 seconds (e.g., at most about 1-5 seconds, etc.). The 1 mL Absorption Time test is described b the test method ASTM D824-86.

According to certain embodiments of the invention, for instance, the composite may have a Spill Absorption Time of less than 20 seconds. In other embodiments, for example, the composite may have a Spill Absorption Time of 15 seconds or less. As such, in certain embodiments, the composite may have a Spill Absorption Time from at most about any of the following: 20, 18, 15, 12, 10, 8, and 5 seconds (e.g., at most about 5-15 seconds, etc.). Spill Absorption Time is a modification of the 1 mL Absorption Time test method where 5 mL of liquid is used rather than 1 mL.

In accordance with certain embodiments of the invention, for instance, the composite may have a Spread Index from about 1 to about 35. In other embodiments, for example, the composite may have a Spread Index from about 1 to 31. As such, in certain embodiments, the composite may have a Spread Index from at least about 1 and/or at most about 35, 34, 33, 32, and 31 (e.g., about 1-31, etc.). Spread Index can be determined right after the end point for the Spill Absorption Time test. It consists of measuring the distance in centimeters between the two farthest points of the wetted area created b the liquid along the MD direction and the CD direction of the sample tested. Those two numbers can be added to produce the index, which reflects the tendency of the liquid to spread.

According to certain embodiments of the invention, for instance, the absorbent nonwoven may have a basis weight from about 30 to about 60 gsm. In other embodiments, for example, the absorbent nonwoven may have a basis weight from about 35 to about 55 gsm. In further embodiments, for example, the absorbent nonwoven may have a basis weight from about 40 to about 51 gsm. As such, in certain embodiments, the absorbent nonwoven may have a basis weight from at least about any of the following: 30, 33, 35, 37, and 40 gsm and/or at most about 60, 57, 55, 53, and 51 gsm (e.g., about 33-55 gsm, about 40-51 gsm, etc.).

Additionally, according to certain embodiments of the invention, for example, the two-layer composite may have a basin weight from about 50 to about 80 gsm. In other embodiments, for example, the two-layer composite may have a basis weight from about 60 to about 70 gsm. In further embodiments, for example, the two-layer composite may have a basis weight from about 65 to about 68 gsm. As such, in certain embodiments, the two-layer composite may have a basis weight from at least about any of the following: 50, 55, 60, 63, and 65 gsm and/or at most about 80, 75, 70, 69, and 68 gsm (e.g., about 60-70 gsm, about 65-68 gsm, etc.).

According to further embodiments of the invention, for instance, the three-layer composite may have a basis weight from about 60 to about 90 gsm. In other embodiments, for example, the three-layer composite may have a basis weight from about 70 to about 80 gsm. In further embodiments, for example, the three-layer composite may have a basis weight from about 71 to about 74 gsm. As such, in certain embodiments, the three-layer composite may have a basis weight from at least about any of the following: 60, 65, 68, 70, and 71 gsm and/or at most about 90, 85, 80, 75, and 74 gsm (e.g., about 65-80 gsm, about 68-74 gsm, etc.).

In accordance with certain embodiments of the invention, for example, the composite may have a linting of less than 5000/cu.ft. In other embodiments, for example, the composite may have a linting of less than 2000/cu.ft. In further embodiments, for instance, the composite may have a linting of less than 500/cu.ft. As such, in certain embodiments, the composite may have a linting from at most about any of the following: 5000, 3000, 2000, 1000, 750, and 500/cu.ft. (e.g., at most about 2000/cu.ft., at most about 500/cu.ft., etc.). Linting can be measured in accordance to the standard test method ISO9073-10:2003 where the samples can be manipulated using the Gelboflex method.

In accordance with certain embodiments of the invention, for instance, the composite may have a Martindale abrasion of less than 100 mg. In other embodiments, for example, the composite may have a Martindale abrasion of less than 50 mg. In further embodiments, for instance, the composite may have a Martindale abrasion of less than 10 mg. As such, in certain embodiments, the composite may have a Martindale abrasion from at most about any of the following: 100, 75, 50, 25, 20, 15, and 10 mg (e.g., about 0-100 mg, about 0-10 mg, etc.). Martindale testing can be run as per ASTM D4966-98 using the Evaluation Option 3 to determine the mass loss. The tests can be performed using 80 cycles and 9 kPa selected as the weight used to set the pressure against each specimen.

FIG. 1 illustrates across sectional view of an absorbent composite according to an embodiment of the invention. As shown in FIG. 1, the composite 1 includes an absorbent nonwoven 102 and a liquid-impermeable film 106 extrusion coated onto the absorbent nonwoven 102. The absorbent nonwoven 102 has a three-dimensional pattern 104. In an embodiment of the invention the three-dimensional pattern 104 may be imaged on an outer surface of the absorbent nonwoven 102. In a preferred embodiment of the invention, the three-dimensional pattern 104 may be imaged through the absorbent nonwoven 102 layer.

For example, according to this preferred embodiment of the invention, the image to be formed throughout the absorbent nonwoven layer may be patterned on an image transfer device. For example, the image transfer device may comprise one or more drums or even on one or more sleeves affixed to a corresponding drum. One or more water jets, for example, high pressure water jets according to an embodiment of the invention, may be applied to a side of the nonwoven opposite to the side contacting the image transfer device. Without intending to be bound by the theory, the one or more water jets and water directed through the nonwoven causes the fibers of the nonwoven to become displaced according to the image on the image transfer device such as the image formed on one or more drums or one or more sleeves affixed to a corresponding drum causing a three-dimensional pattern 104 to be imaged throughout the nonwoven according to such image. Such imaging techniques are further described in, for example, U.S. Pat. No. 6,314,627 entitled "Hydroentangled Fabric having Structured Surfaces"; U.S. Pat. No. 6,735,833 entitled "Nonwoven Fabrics having a Durable Three-Dimensional Image"; U.S. Pat. No. 6,903,034 entitled "Hydroentanglement of Continuous Polymer Filaments"; U.S. Pat. No. 7,091,140 entitled "Hydroentanglement of Continuous Polymer Filaments"; and U.S. Pat. No. 7,406,755 entitled "Hydroentanglement of Continuous Polymer Filaments" each of which are included in their entirety herein by reference. An "imaged nonwoven" may be further used herein to define the use of such imaging techniques. In a preferred embodiment of the invention, without intending to be bound by theory, the absorbent nonwoven 102 or image nonwoven imaged with a three-dimensional pattern 104 at least one of improves liquid absorption and reduces liquid run-off.

Figure 2:
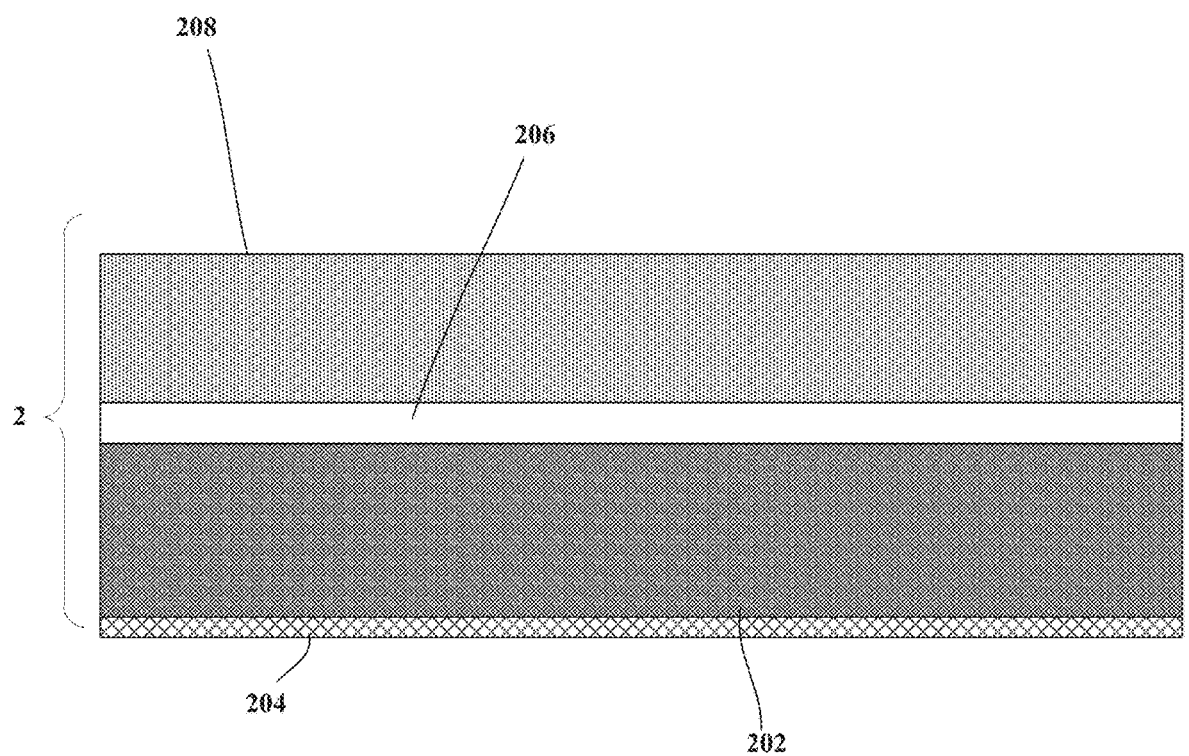
FIG. 2 illustrates a cross-sectional view of an absorbent composite according to an embodiment of the invention.

FIG. 2, for example, illustrates a cross sectional view of an absorbent composite according to an embodiment of the invention. As shown in FIG. 2, the composite 2 includes an absorbent nonwoven 202, a second nonwoven 208, and a liquid-impermeable film 206 that is extrusion coated between the absorbent nonwoven 202 and the second nonwoven 208. The absorbent nonwoven 202 may be an imaged nonwoven that is imaged with a three-dimensional pattern 204. In a preferred embodiment of the invention, without intending to be bound by theory, the absorbent nonwoven 202 imaged with a three-dimensional pattern 204 at least one of improves liquid absorption and reduces liquid run-off.

In another aspect of the invention, the composite includes an absorbent nonwoven comprising a hydroentangled composite. The hydroentangled composite may comprise a layer of cellulose fiber positioned between two nonwoven webs. According to an embodiment of the invention, the composite may also comprise a liquid-impermeable film.

In accordance with certain embodiments of the invention, for example, one or both of the nonwoven webs may comprise a spunbond web. In addition, for instance, one or both nonwoven webs may further comprise a meltblown layer. According to certain embodiments of the invention, one or both of the nonwoven webs may be a SPINLACE nonwoven fabric as described in, for example, U.S. Pat. Nos. 6,903,034 and 7,091,140 already referenced herein; and U.S. Pat. No. 7,455,800 entitled "Hydroentanglement of Continuous Polymer Filaments" which is also fully incorporated herein by reference. In certain embodiments of the invention, one or both of the nonwoven webs may comprise a nanofiber, or, alternatively, may include a nanofiber layer.

In accordance with certain embodiments of the invention, the absorbent nonwoven may comprise a three-dimensional pattern. Without intending to be bound by theory, an absorbent nonwoven having a three-dimensional pattern may one or both of improve liquid absorption and reduce liquid run-off.

In accordance with certain embodiments of the invention, for instance, the layer of cellulose fiber may be air-laid. In other embodiments, for example, the layer of cellulose fiber may be wet-laid. In further embodiments, for instance, the layer of cellulose fiber may comprise a tissue paper. According to certain embodiments, the layer of cellulose fiber may comprise a layer of wood pulp fiber.

In accordance with certain embodiments of the invention, for example, the liquid-impermeable film may comprise a breathable polymer film. In some embodiments, for instance, the liquid-impermeable film may comprise at least one hygroscopic polymer. In some embodiments, for example, the liquid-impermeable film may comprise at least one polyolefin polymer and combinations thereof. In further embodiments, for instance, the liquid-impermeable film may comprise at least one of polyethylene, ethylene-vinyl acetate, ethyl methyl acrylate, polypropylene, plastomer or elastomeric polyolefin (e.g., VISTAMAXX™ from Exxon-Mobil Chemical Company, VERSIFY™ and AFFINITY™ from The Dow Chemical Company), thermoplastic urethane, polyether block amide copolymer (e.g., PEBAX® from Arkema Group), copolyester thermoplastic elastomer (e.g., ARNITEL® resin from DSM Engineering Plastics, HYTREL® from E.I. Dupont de Nemours and Company), and combinations thereof. According to certain embodiments, the film may comprise an extrusion coated film.

According to certain embodiments of the invention, for example, the composite may have a normalized absorbency from about 5 to about 20. In other embodiments, for instance, the composite may have a normalized absorbency from about 8 to about 18. In further embodiments, for example, the composite may have a normalized absorbency from about 10 to about 15. As such, in certain embodiments, the composite may have a normalized absorbency from at least about any of the following: 5, 8, and 10 and/or at most about 20, 18, and 15 (e.g., about 5-20, about 10-18, etc.). Composite Normalized Absorbency is an index developed by first measuring the weight of water absorbed by sq. meter of composite as per the Absorption Capacity test and dividing that number by the weight per sq. meter of the absorbent nonwoven layer used in the composite.

In accordance with certain embodiments of the invention, for instance, the composite may have a 1 mL Absorption Time of less than 10 seconds. In other embodiments, for example, the composite may have a 1 mL Absorption Time of less than 5 seconds. As such, in certain embodiments, the composite may have a 1 mL Absorption Time from at most about any of the following: 10, 9, 8, 7, 6, 5, and 1 seconds (e.g., at most about 1-5 seconds, etc.). The 1 mL Absorption Time test is described by the test method ASTM D824-86.

According to certain embodiments of the invention, for instance, the composite may have a Spill Absorption Time of less than 20 seconds. In other embodiments, for example, the composite may have a Spill Absorption Time of 15 seconds or less. As such, in certain embodiments, the composite may have a Spill Absorption Time from at most about any of the following: 20, 18, 15, 12, 10, 8, and 5 seconds (e.g., at most about 5-15 seconds, etc.). Spill Absorption Time is a modification of the 1 mL Absorption Time test method where 5 mL of liquid is used rather than 1 mL.

According to certain embodiments of the invention, for instance, the absorbent nonwoven may have a basis weight from about 20 to about 50 gsm. In other embodiments, for example, the absorbent nonwoven may have a basis weight from about 25 to about 45 gsm. In further embodiments, for example, the absorbent nonwoven may have a basis weight from about 33 to about 42 gsm. As such, in certain embodiments, the absorbent nonwoven may have a basis weight from at least about any of the following: 20, 23, 25, 30, and 33 gsm and/or at most about 50, 47, 45, 43, and 42 gsm (e.g., about 23-47 gsm, about 33-42 gsm, etc.).

Additionally, according to certain embodiments of the invention, for example, the composite may have a basis weight from about 50 to about 70 gsm. In other embodiments, for example, the composite may have a basis weight from about 55 to about 65 gsm. In further embodiments, for example, the composite may have a basis weight from about 60 to about 64 gsm. As such, in certain embodiments, the composite may have a basis weight from at least about any of the following: 50, 53, 55, 57, and 60 gsm and/or at most about 70, 68, 66, 65, and 64 gsm (e.g., about 55-66 gsm, about 60-64 gsm, etc.).

In accordance with certain embodiments of the invention, for instance, the composite may have a liming of less than 5000/cu.ft. In other embodiments, for example, the composite may have a linting of less than 3000/cu.ft. As such, in certain embodiments, the composite may have a liming from at most about any of the following: 5000, 4500, 4000, 3500, and 3000/cu.ft. (e.g., at most about 0 to about 3000/cu.ft., etc.). Linting can be measured in accordance to the standard test method ISO9073-10:2003 where the samples can be manipulated using the Gelboflex method.

In accordance with certain embodiments of the invention, for instance, the composite may have a Martindale abrasion of less than 50 mg. In other embodiments, for example, the composite may have a Martindale abrasion of less than 25 mg. In further embodiments, for instance, the composite may have a Martindale abrasion of less than 15 mg. As such, in certain embodiments, the composite may have a Martindale abrasion from at most about any of the following: 35, 25, 20, and 15 mg (e.g., about 0-15 mg, about 0-50 mg, etc.). Martindale testing can be run as per ASTM D4966-98 using the Evaluation Option 3 to determine the mass loss. The tests can be performed using 80 cycles and 9 kPa selected as the weight used to set the pressure against each specimen.

Figure 3:
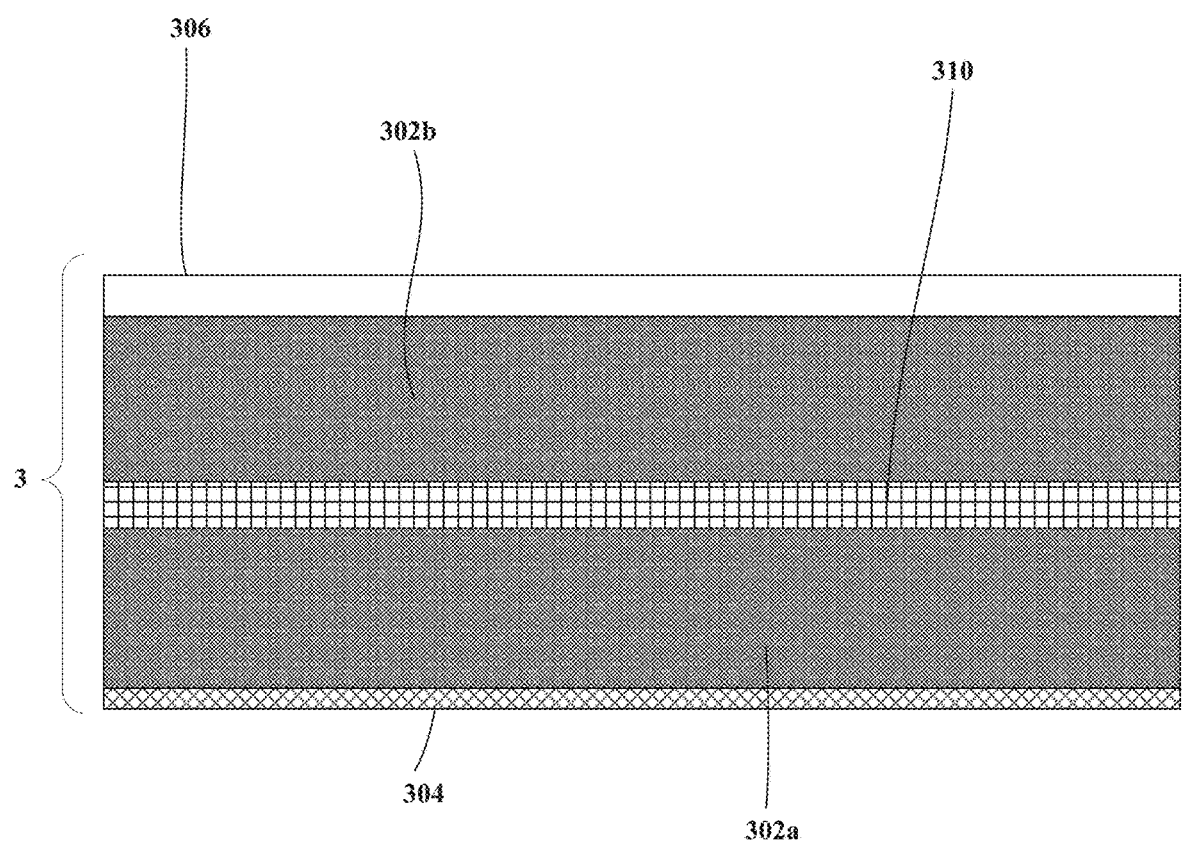
FIG. 3 illustrates a cross-sectional view of an absorbent composite according to an embodiment of the invention.

For example, FIG. 3 illustrates a cross sectional view of an absorbent composite according to an embodiment of the invention. As shown in FIG. 3, the composite 3 includes two absorbent nonwovens 302*a*, 302*b* with a layer of cellulose fiber 310 positioned between the two absorbent nonwovens 302*a*, 302*b*. As shown in this exemplary embodiment of the invention, the composite 3 also includes a liquid-impermeable film 306 extrusion coated onto one of the absorbent nonwovens 302*b*. The absorbent nonwoven 302*a* without the liquid-impermeable film 306 is an imaged nonwoven having a three-dimensional pattern 304. Without intending to be bound by theory, the absorbent nonwoven 302*a* imaged with a three-dimensional pattern 304 may improve liquid absorption and reduce liquid run-off of the composite 3.

II. Process for Forming a Composite

In another aspect, certain embodiments of the invention provide a process for forming a composite. The process may comprise hydroentangling a nonwoven material comprising at least one spunbond web to form an absorbent nonwoven, and extrusion coating a liquid-impermeable film onto a surface of the absorbent nonwoven.

In accordance with certain embodiments of the invention, for example, the liquid-impermeable film may comprise a breathable polymer film. In some embodiments, for instance, the liquid-impermeable film may comprise at least one hygroscopic polymer. In other embodiments, for example, the liquid-impermeable film may comprise at least one polyolefin polymer and combinations thereof. In further embodiments, for instance, the liquid-impermeable film may comprise at least one of polyethylene, ethylene-vinyl acetate, ethyl methyl acrylate, polypropylene, plastomer or elastomeric polyolefin (e.g., VISTAMAXX™ from Exxon-Mobil Chemical Company, VERSIFY™ and AFFINITY™ from The Dow Chemical Company), thermoplastic urethane, polyether block amide copolymer (e.g., PEBAX® from Arkema Group), copolyester thermoplastic elastomer (e.g., ARNITEL® resin from DSM Engineering Plastics, HYTREL® from E.I. Dupont de Nemours and Company), and combinations thereof. According to certain embodiments, the film may comprise an extrusion coated film.

In accordance with an embodiment of the invention, the process may further comprise melt-spinning a polymer composition and forming the at least one spunbond web. In other embodiments, the process may further comprise forming the polymer composition. Further pursuant to this embodiment, for example, the polymer composition may comprise at least one of polyolefins, polyesters, polyamides, and combinations thereof. In some embodiments, for instance, the polymer composition may comprise at least one of polyethylene, polypropylene, partially aromatic or fully aromatic polyesters (e.g., polyethylene terephthalate), polyhexamethylene diadipamide, polycaprolactam, aromatic or partially aromatic polyamides, aliphatic polyamides, and combinations thereof. In other embodiments, for example, the polymer composition may comprise at least one of polypropylene, partially aromatic or fully aromatic polyesters (e.g., polyethylene terephthalate), and combinations thereof. In further embodiments, for instance, the polymer composition may comprise polypropylene. In other embodiments, for example, the polymer composition may comprise partially aromatic or fully aromatic polyesters (e.g., polyethylene terephthalate). In further embodiments, for instance, the polymer composition may comprise polyethylene terephthalate.

According to certain embodiments of the invention, the step of forming the polymer composition may further comprise forming a first and a second polymer composition and the process may further comprise meltspinning the first and second polymer composition through a die for forming bicomponent fibers, such as a bicomponent fiber having a sheath and a core. Further pursuant to this embodiment, for example, the sheath may comprise a polyolefin. In some embodiments, for instance, the sheath may comprise at least one of polyethylene or polypropylene. In further embodiments, for example, the sheath may comprise polyethylene. According to certain embodiments, for instance, the core may comprise at least one of a polyolefin or polyester. In some embodiments, for example, the core may comprise at least one of polyethylene, polypropylene, polyester, and combinations thereof. In further embodiments, for instance, the core may comprise at least one of polypropylene or polyester.

In accordance with certain embodiments of the invention, the process may further comprise positioning a first side of the absorbent nonwoven directly or indirectly onto an image transfer device having a three-dimensional pattern and applying jets of fluid directly or indirectly to a second side of the absorbent nonwoven to impart a three-dimensional pattern onto the absorbent nonwoven. Further pursuant to this embodiment, for example, imaging the absorbent nonwoven with a three-dimensional pattern may improve liquid absorption and reduce liquid run-off.

In accordance with certain embodiments of the invention, the process may further comprise attaching a second nonwoven web, in which the liquid-impermeable film is positioned between the absorbent nonwoven and the second nonwoven web. Further pursuant to this embodiment, for example, the second nonwoven may comprise at least one spunbond layer. Alternatively or in addition, for instance, the second nonwoven may comprise at least one meltblown layer. Alternatively or in addition, for example, the second nonwoven may comprise at least one nanofiber layer. In further embodiments, for instance, the second nonwoven may comprise a non-absorbent nonwoven.

According to certain embodiments of the invention, for example, the at least one absorbent nonwoven may comprise at least two spunbond webs. In accordance with certain embodiments of the invention, the process may further comprise depositing a layer of cellulose fiber indirectly of directly between the at least two spunbond webs to provide the nonwoven material, and hydroentangling the nonwoven material to form the absorbent nonwoven. Further pursuant to this embodiment, for example, the layer of cellulose fiber may comprise a layer of wood pulp fiber. Even further pursuant to this embodiment, the wood pulp fiber may additional comprise short synthetic fibers. For example, the layer of wood pulp fiber may comprise less than about 0.5% by weight of short synthetic fibers, less than about 1% by weight of short synthetic fibers, less than about 2% by weight of short synthetic fibers, less than about 5% by weight of short synthetic fibers, less than about 10% by weight of short synthetic fibers, less than about 15% by weight of short synthetic fibers, less than about 20% by weight of short synthetic fibers, less than about 25% by weight of short synthetic fibers, or less than about 35% by weight of short synthetic fibers, less than about 40% by weight of short synthetic fibers, or less than about 50% by weight of short synthetic fibers.

In some embodiments, for example, the step of depositing the layer of cellulose fiber between the at least two spunbond webs may comprise air laying the layer of cellulose fiber. In other embodiments, for instance, the step of depositing the layer of cellulose fiber between the at least two spunbond webs may comprise wet laying the layer of cellulose fiber. In further embodiments, for example, the step of depositing the layer of cellulose fiber between the at least two spunbond webs may comprise introducing a tissue paper.

According to certain embodiments of the invention, the absorbent nonwoven may be hydrophilic. Further pursuant to this embodiment, the polymer composition may further comprise a surfactant. For instance, the polymeric composition may include a hydrophilic additive (e.g., surfactant), rendering the formed absorbent nonwoven hydrophilic. Further to these embodiments, a binder may be included with the hydrophilic additive. Alternatively or in addition, the absorbent nonwoven may comprise a topical surfactant (e.g., a topical hydrophilic surfactant) to render the absorbent nonwoven hydrophilic. In some embodiments, the absorbent nonwoven may be treated with a topical surfactant (e.g., a topical hydrophilic surfactant) after being imaged with a three-dimensional pattern. In certain embodiments, for instance, the inclusion of surfactant molecules either in the polymer composition or as a topical treatment (e.g., a topical hydrophilic surfactant) of the absorbent nonwoven may increase wettability of the absorbent nonwoven.

Figure 4:
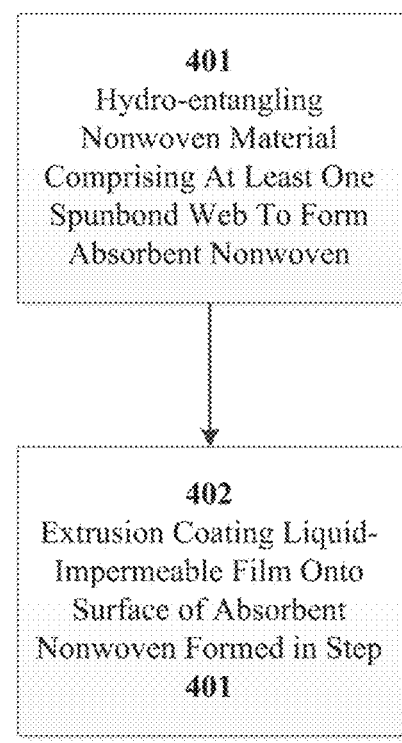
FIG. 4 illustrates a process flow diagram for forming an absorbent composite according to an embodiment of the invention.

For example, FIG. 4 illustrates a process flow diagram for forming an absorbent composite according to an embodiment of the invention. As shown in FIG. 4, the process comprises hydroentangling a nonwoven material comprising at least one spunbond web to form an absorbent nonwoven in step 401. The process further comprises step 402, which comprises extrusion coating a liquid-impermeable film onto a surface of the absorbent nonwoven formed in step 401. Of course, other methods otherwise known to an ordinary skilled artisan may be used to dispose the liquid-impermeable film onto the absorbent nonwoven.

Thus, the invention includes, in accordance with certain embodiments of the invention, a cost-effective absorbent nonwoven based, at least in part, on a spunbond web with a film extrusion coated on the absorbent nonwoven, such composite exhibiting a superior absorbency, an acceptable abrasion resistance, and low linting.

According to certain embodiments of the invention, any one or more of the layers of the composite may comprise an antimicrobial. Without intending to be bound by theory, an antimicrobial-laced composite may be useful in infection control applications. The antimicrobial may any of be disposed in the material of the layer, included at the surface of the layer, or any combination thereof.

In a non-limiting example, the composite may comprise an antimicrobial nonwoven layer. In an embodiment of the invention the antimicrobial may be disposed on the nonwoven material. For example, metals or metal-based compounds having antimicrobial properties may be deposited on and/or disposed in the nonwoven material. Non-limiting examples of metals include copper or silver. For example, copper alloys include, but are not limited to, Cu-OFE, Cu-OF, CuAgO,04(OF), Cu-ETP, Cu-FRHC, Cu-ETP-1, CuAgO04, CuAgO,07, CuAgO,10, Cu-DLP, CuAgO,10P, Cu-DHP, Cu—C, Cu-DHP, Cu-FRTP, CuTeP, CuZr, CuCd1, 0, CuBe1,7, CuBe2, CuCo2Be, CuNi2Be, CuMgO5, CuNi1 P, CuFe2P, CuZn5, CuZn1 0, CuZn1 5, CuZn20, CuZn28, CuZn30, CuZn30As, CuZn36, CuZn40, CuSn3Zn9, CuZn1 9Sn, CuZn28Sn1As, CuSn5, CuSn4, CuSn6, CuSn8, CuAI8Fe3, CuAM OFe1, CuAI10Ni5Fe4, CuAI10Ni5Fe-4, CuMnl 1A18Fe3Ni3-C, CuSi1, CuSi3Mn1, CuSi3Mn1, CuZn20AI2As, CuZn1 3AI1 Ni1 Si1, CuNi3Si1, CuNi1 Si, CuNi1 0Fe1 Mn, CuNi1 0Fe1 Mn, CuNi1 0Fe1 Mn1-B, CuNi25, CuNi30Mn1 Fe, CuNi30Mn1 Fe, CuNi30Fe2Mn2, CuNi9Sn2, CuNi18Zn20, CuNi1 2Zn24, Cu—C, Cu-OF, Cu—C, Cu—C, CuSn12-B, CuAI10Fe2-B, CuAI10Fe2-B, CuAI10Ni5Fe4, CuAI10Fe5Ni5-B, CuMn1 1AI8Fe3Ni3-C, CuAI10Fe5Ni5-B, CuNi10Fe1 Mn1-B, CuNi30Fe1Mn1 NbSi—C, Cu-OFE, Cu-OF, CuAgO,05(OF), CuAgO,05 (OF), CuAgO,05(OF), Cu-ETP, Cu—FRHC, CuAgO,05, CuAgO.1, Cu-DLP, CuAgO,1 (P), Cu-DHP, Cu-FRTP, CuTe (P), CuCd1, CuBe1.7, CuBe2, CuCo2Be, CuNi2Be, CuZn5, CuZnI O, CuZn15, CuZn15, CuZn20, CuZn30, CuZn30As, CuZn40, CuZn28Sn1, CuSn5, CuSn4, CuSn6, CuSn8, CuAI8Fe3, CuAM 0Ni5Fe4, CuAM 0Ni5Fe4, CuSi1, CuSi3Mn1, CuZn20AI2, CuNi1 Si, CuNi10Fe1 Mn, CuNi25, CuNi30Mn1 Fe, CuNi30Mn1 Fe, CuNi30Fe2Mn2, CuNi9Sn2, CuNi18Zn20, CuNi12Zn24, Cu—OF, CuAI10Ni5Fe4, CuAI7Si2, CuCM Zr, CuNi10Zn42Pb2, CuNi2Si, CuSnO CuSn5Zn5Pb5-C, CuPb5Sn5Zn5, CuZn30As, CuZn33Pb2-C, CuZn36Pb2As, CuZn36Pb2As, CuZn36Pb2As, CuZn36Pb3, CuZn36Pb3, CuZn36Sn1 Pb, CuZn37, CuZn37Pb2, CuZn38Pb2, CuZn40Pb2, CuZn39Pb1, CuZn39Pb2, CuZn39Pb3, CuZn39Pb4, CuZn39Sn1, CuZn38Sn1, CuZn40Mn1Ph1 FeSn, CuZn40Pb2, CuSn4Pb4Zn3, CuZn39Pb1AI—C, CuZn40Mn1 Pb1AIFeSn and/or CuZn43Pb2AI.

There are a number of antimicrobial compounds known in the art that may be disposed in a nonwoven web and/or film of a composite. For example, the MICROBAN® antimicrobial additives (e.g., triclosan-based antimicrobials, silver ion-based antimicrobials, zinc-based antimicrobials, quaternary ammonium-based antimicrobials, etc), available from Microban International, Ltd. having a place of business in Huntersville, N.C.

Organic-based antimicrobials may be dispersed into a polymer of a nonwoven that bloom to the surface of the fiber overcoming the limitation of lower surface concentration associated with metal-based antimicrobial additives. For example, Triclosan that is dispersed into a polymeric formulation blooms to the surface as the polymer is extruded into a fiber.

The antimicrobial may comprise an antimicrobial heat labile component in combination with a carrier. In certain embodiments of the invention, the concentration of the antimicrobial at the surface of the fiber may be from about 10 wt % to about 50 wt % based upon the total weight of the fiber. Additionally, the concentration of the antimicrobial at the center of the fiber may be less than about 50% of the concentration of the antimicrobial at the surface of the fiber.

In certain embodiments of the invention, the nonwoven layer may comprise a bicomponent fiber defined by a sheath and a core, wherein the concentration of the antimicrobial in the sheath is greater than the concentration of the antimicrobial in the core. For example, according to certain embodiments of the invention, the concentration of the antimicrobial in the sheath may be from about 13 wt % to about 45 wt % based upon the total weight of the fiber. The concentration of the antimicrobial in the core is about 50% of the concentration of the antimicrobial in the sheath, according to certain embodiments of the invention.

In certain embodiments of the invention, an antimicrobial heat labile component may comprise any of didecyldimethyl ammonium chloride, quaternary ammonium compounds, benzyl C-12-16 alkylidimethyl chlorides, benzathonium chloride, cetrimonium chloride, N-(3-aminopropyl)-N-dodecylpropane-1,3 diamine, and any combination thereof. In certain embodiments of the invention, the antimicrobial heat labile component may comprise from about 0 wt % to about 30 wt % of didecyldimethyl ammonium chloride, from about 0 wt % to about 22 wt % of quaternary ammonium compounds, from about 0 wt % to about 22 wt % of benzyl C-12-16 alkylidimethyl chlorides, from about 1 wt % to about 22 wt % of benzathonium chloride, from about 1 wt % to about 22 wt % of cetrimonium chloride, and from about 1 wt % to about 22 wt % of N-(3-aminopropyl)-N-dodecylpropane-1,3 diamine. According to a specific embedment of the invention, the antimicrobial heat labile component may comprise about 30 wt % of didecyldimethyl ammonium chloride, 22 wt % of benzyl C-12-16 alkylidimethyl chlorides, 17 wt % of benzathonium chloride, 9 wt % of cetrimonium chloride, 22 wt % of N-(3-aminopropyl)-N-dodecylpropane-1,3 diamine. According to another specific embodiment of the invention, the antimicrobial heat labile component may comprise about 30 wt % of didecyldimethyl ammonium chloride, 22 wt % of quaternary ammonium compounds, 17 wt % of benzathonium chloride, 9 wt % of cetrimonium chloride, 22 wt % of N-(3-aminopropyl)-N-dodecylpropane-1,3 diamine.

According to an embodiment of the invention, any of a nonwoven layer and combinations thereof and/or the film of the composite of the invention may comprise an antimicrobial additive that includes any one of or any combination of the antimicrobials disclosed herein or otherwise known in the art.

EXAMPLES

The present disclosure is further illustrated by the following examples, which in no way should be construed as being limiting. That is, the specific features described in the following examples are merely illustrative and not limiting.

Test Methods

Basis weight was measured in accordance with standard test method ASTM D3776.

Strip tensile strength was measured in accordance with standard test method EN 29073-3 using a 5 mm wide strip.

Peel strength of the bond between the film and the absorbent nonwoven was measured in accordance with the standard test method AATCC 136.

Hydrohead test is a measure of web impermeability and consists of building a pressure of liquid against the sample and recording the pressure at which 3 droplets are observed on the opposite side. The test was performed in accordance with standard test method IST 80.6.

Run-off test method measures the absorbency of a web and consists of measuring the quantity of test liquid (e.g., simulated urine) which runs down a nonwoven test piece when a specified mass of test liquid is poured onto the nonwoven test piece superimposed on a standard absorbent media and placed on an inclined plane. The results are reported as % of liquid that ran-off the sample. This test was performed in accordance with standard test method ISO 9073-11.

1 mL Absorption Time test measures the time needed for a web to absorb 1 mL of deionized or distilled water, the end point being when the water reflection or shine disappears from the surface of the web where the liquid was applied. This test is described by the test method ASTM D824-86.

Spill Absorption Time is a modification of the 1 mL Absorption Time test method where 5 mL of liquid was used rather than 1 mL.

Spread index was determined right after the end point for the Spill Absorption Time test. It consisted of measuring the distance in centimeters between the two farthest points of the wetted area created by the liquid along the MD direction and the CD direction of the sample tested. Those two numbers were added to produce the index, which reflects the tendency of the liquid to spread.

Absorption Capacity measured the total absorbency of the composite or the absorbent layer being tested after immersing such composite or absorbent layer in water and allowing it to drain for a pre-determined amount of time. The results reflect the amount of water absorbed as % of the weight of the product tested. This test was performed in accordance with the standard test method ISO 9073-6.

Composite Normalized Absorbency is an index developed by first measuring the weight of water absorbed by sq. meter of composite as computed from the Absorption Capacity test performed on the composite and by dividing that number expressed as grams of water by the weight per square meter of the absorbent nonwoven layer used in the composite. The Normalized Absorbency is represented b weight of water (e.g., in grams) absorbed per weight of material in the absorbent nonwoven layer measured in the same dimensional units as the weight of water.

Static decay measures the ability of the composite to dissipate a static charge by measuring the time needed to do so. This test was performed in accordance with standard test method IST 40-2.

Pin-hole testing consisted of acquiring a sample that is about 2.5 sq. meters (i.e., 3 sq. yards), laying it on a flat surface covered by a white absorbent paper or textile, making a 50% isopropyl alcohol solution containing methylene blue, using a paint roller to spread the solution over the 2.5 sq. meter area of the sample, and, immediately after, rolling back or removing the sample and identifying the stains on the white background, each stain representing a pinhole. This test was repeated for 3 samples. When completed, the number of pinholes was added, and the total area of sample tested was measured. Using this information, the number of pinholes per sq. meter was computed.

Martindale testing was run as per ASTM D4966-98 using the Evaluation Option 3 to determine the mass loss. The tests were performed using 80 cycles, and 9 kPa was selected as the weight used to set the pressure against each specimen.

Linting measured the tendency of a web to shed particles when manipulated. This tendency was measured in accordance to the standard test method ISO9073-10:2003 where the samples were manipulated using the Gelboflex method.

Comparative Example 1

This commercial laminate, known as 7070 L, consisted of two nonwovens glued respectively on each side of a film. The absorbent nonwoven glued to one side was a 30 gsm spunbond made on a double beam REICOFIL®-2 spunbond line Reifenhäuser GmbH & Co. KG Maschinenfabrik, Spicher Straße 46, 53844 Troisdorf, Deutschland) using atypical 35 MFR polypropylene blended with green pigment concentrate. The fabric was point bonded using a calender and was topically treated with a solution that left on the nonwoven about 0.8% solid add-on of a hydrophilic surfactant identified as PATWET-70 (Apollo Chemical Co., 2001 Willow Springs Lane, Budington, N.C. USA), which is a proprietary anionic surfactant that is used in the textile industry and provided in liquid form having a specific gravity of 1.1 g/ml at 25° C. and is soluble in water. The other nonwoven consisted of a SMS type nonwoven made of polypropylene and having a basis weight of 15 gsm. Those nonwovens were respectively glued with discontinuous layers of pressure sensitive adhesive glue to the film. The film was cast using a typical co-extrusion line able to make an A/B film; however, for this example both extruders were fed the same composition, thereby simulating a monolayer film. The composition of the film consisted of 71.4% of a linear low density polypropylene identified as 1002KW, which is a linear low density butene copolymer of ethylene (LLDPE) (sold by ExxonMobil Chemical Company, 13501 Katy Freeway, Houston, Tex. 77079-1398) having a melt index of 2.0 g/10 min @ 190 C under a load of 2.16 kg. The composition also included 23.8% of a typical low density polyethylene (LDPE) having a density of 0.921 g/cm3 and a melt index of 1.9 g/10 min @ 190 C under a load of 2.16 kg. Finally, the composition also included 4.8% of a green pigment concentrate. Further pursuant to these embodiments, a binder may be included with these additives.

Comparative Example 2

A 36 gsm spunbond made on a 2-beam spunbond line produced by STP Impianti S.p.A, (STP Impianti S.p.A., Via Ronchi 16/18-20027 Rescaldina, Milan, Italy) using a typical 35 MFR polypropylene was topically coated with a solution that left about 0.9% solid add-on of PATWET-70. This nonwoven was extrusion coated with a 20 gsm blue film. The film was extruded using a typical 2-layer co-extrusion coating line. For this experiment, the composition fed by the two extruders feeding respectively the A & B side of the die had the same formulation and were used in similar process conditions. The composition of the film was 2 parts of Dow ELITE™ 5815, an enhanced polyethylene having a melt index of 15 g/10 min @ 190 C under a load of 2.16 kg (sold by The Dow Chemical Company, 2030 Dow Center, Midland, Michigan USA 48674), 1 part of an extrusion grade LLDPE having a MI of 2 (sold by Saudi Basic Industries Corporation, P.O. Box 5101, Riyadh 11422, Kingdom of Saudi Arabia, under the name 218), 1 part of a typical LDPE used for extrusion coating having a NH of 1.9 g/10 min, and 6% of a blue color masterbatch.

Example 1

A single layer of spunbond made on a 2-beam STP Impianti spunbond production line was hydroentangled on a pilot line, producing a nominal 40 gsm web. During that process, the spunbond was first hydroentangled on a flat belt using moderate pressure, and then it was again hydroentangled at a speed of 60 fpm while being in contact with an image transfer sleeve. In that second operation three strips were used with respective and increasing pressures of 1400 and 3500 psi. When a spunbond is hydroentangled at these pressures, several of the bond points are broken, thereby allowing the substantially continuous filaments to be entangled and forming a knot. For this sample the image transfer sleeve used produced a pattern having good resistance to abrasion as tested by the Martindale test method. This hydroentangled fabric was subsequently treated by padding the web with a solution comprising PATWET-70 and subsequently dried using steam cans, leaving about 0.9% solid add-on of surfactant. Finally, nonwoven was extrusion coated with a 20 gsm film of the same composition as the film in Comparative Example 2 using the same process as Comparative Example 2.

Example 2

A single layer of spunbond made on a 2-beam STP Impianti spunbond production line was hydroentangled on a pilot line, producing a nominal 50 gsm web. During that process, the spunbond was first hydroentangled on a flat belt using moderate pressure, and then it was again hydroentangled at a speed of 60 fpm while being in contact with an image transfer sleeve. In that second operation, three strips were used with respective and increasing pressures of 1400 and 3500 psi. For this sample the image transfer sleeve used produced a pattern having good resistance to abrasion as tested by the Martindale test method. This hydroentangled fabric was subsequently treated by padding the web with a solution comprising PATWET-70 and subsequently dried using steam cans, leaving about 0.9% solid add-on of surfactant. Finally, this nonwoven was extrusion coated with a 20 gsm film of the same composition as the film in Comparative Example 2 using the same process as Comparative Example 2.

Example 3

A composite was made from 2 layers of 10 gsm spunbond made on a single beam REICOFIL®-2 line from Reifenhäuser GmbH & Co. KG Maschinenfabrik and about 20 gsm of wood pulp fiber airlaid positioned between the two spunbond layers prior to hydro-entanglement. The process consisted of first lightly entangling the composite on a flat bed, then further hydroentangling it on an image transfer sleeve using pressure that produced good image definition without washing away the wood pulp fibers. Here, the maximum hydro-entanglement wafer jet pressure was substantially lower than for Examples 1 and 2 because such high pressure would have washed away the wood pulp fibers. The hydroentangled composite was dried and topically treated with a solution comprising PATWET-70 and subsequently dried using steam cans, leaving about 0.9% solid add-on of surfactant.

TABLE 1

| Test Method | Unit | Comparative Sample 1 | Comparative Sample 2 | Sample 1 | Sample 2 | Sample 3 |
|---|---|---|---|---|---|---|
| Basis weight for composite | gsm | 67.5 | 57 | 68 | 73.5 | 63.5 |
| Basis weight of absorb. nonwoven | gsm | ~30 | ~38 | ~40 | ~51 | ~40 |
| Strip Tensile Strength - MD/CD | N/5 cm | 123.0/70.5 | 111.0/57.5 | 70.0/25.5 | 59.0/30.0 | 47.5/26.5 |
| MD Peel Strength | lb | 0.9 | 0.05 | 0.25 | 0.4 | 0.15 |
| Pin-Hole | #/m$^2$ | 0 | 0 | 0 | 0 | — |
| Hydrohead | cm | 144 | 228 | 143 | 138 | 135 |
| Run-off | % | 67.5 | 88 | 55 | 52 | 58 |
| Absorption Capacity tested on treated absorbent layer | % | 678 | 590 | 1110 | 1210 | 1120 |
| Absorption Capacity tested on the composite | % | 436 | 348 | 657 | 802 | 709 |
| Normalized Absorbency | g/g | 9.8 | 5.2 | 11.2 | 11.5 | 11.2 |
| 1 mL Absorption time for treated absorbent layer | sec | 12 | 15.3 | 4.0 | 4.3 | 5.0 |
| 1 mL Absorption Time for composite | sec | 5 | 25 | 4.7 | 3.3 | 5 |
| Spill Absorption Time for composite | sec | 56 | 88 | 15 | 6 | 11 |
| Spread Index for composite | | 42 | 48 | 31 | 26 | 30 |
| Martindale abrasion of absorbent nonwoven | mg | 0.3 | | 8 | 57 | 7 |
| Martindale abrasion of composite | mg | 3.9 | 0.55 | 7.8 | 85 | 12 |
| Linting of absorbent web alone | Number/cu.ft. | 918 | 435 | 818 | 334 | 3700 |
| Linting of composite | Number/cu. Ft. | 590 | 210 | 460 | 1010 | 2620 |

TABLE 1-continued

| Test Method | Unit | Comparative Sample 1 | Comparative Sample 2 | Sample 1 | Sample 2 | Sample 3 |
|---|---|---|---|---|---|---|
| Static decay of treated absorbent layer | Sec | | 19 | 11.5 | 7.5 | 1.55 |
| Static decay composite | Sec | 2.8 | 24 | 5.8 | 14.7 | 0.5 |

The results summarized in Table 1 illustrate that a lower-cost composite can be produced by extrusion coating a film on a spunbond-based absorbent layer rather than through glue lamination. Table 1 further illustrates that the composite can achieve or exceed the liquid handling performance of a glue laminated product while still achieving acceptable mechanical and linting performance.

Comparative Example 2 demonstrates that extrusion coating a spunbond produces a composite with reduced absorption when compared to Comparative Example 1 as illustrated by the Absorption Capacity and Normalized Absorbency results. The slow absorption rate for Comparative Example 2 is also well illustrated by the Run-off, 1 mL Absorption Time, and Spill Absorption Time results when compared to similar test results for Comparative Example 1.

However, when a spunbond was first hydroentangled prior to extrusion coating of the film, the results are different. Examples 1 and 2 show higher Absorption Capacity and Normalized Absorbency results when compared to Comparative Example 1. In regard to absorption rate, Examples 1 and 2 are also faster than Comparative Example 1 at absorbing water as per the 1 mL Absorption Time and Spill Absorption Time tests and absorbing more of the fluid when tested using the Run-off test. Finally, the spill spread as measured by the Spread Index was less for Examples 1 and 2 than for Comparative Example 1.

The higher absorbency of Examples 1 and 2 as well as their ability to acquire the fluid faster and retain it in a smaller area are advantages that should reduce the risk of contamination when such composites are used as sorbent drapes in a surgical procedure. Furthermore, the mechanical properties, abrasion resistance, and liming characteristics of Examples 1 and 2 are suitable for use as sorbent drapes.

In Example 3 a layer of wood pulp was combined with two thin spunbond layers prior to hydro-entanglement. The water pressure during hydro-entanglement was less than for Examples 1 and 2, and, as a result, the spunbond layers retained more of their original structure. However, this structure was compensated for by the presence of wood pulp, a very absorbent product that was tied down in the composite through hydro-entanglement. Example 3 demonstrated good performance in regard to Absorption Capacity, Normalized Absorbency, 1 mL Absorption Time, Run-off, Spill Absorption Time, and Spread Index. Example 3, however, did exhibit a higher level of tinting than Examples 1 and 2.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A two-layered composite, comprising:
    (a) a first layer that is an absorbent nonwoven consisting of a plurality of synthetic fibers rendered hydrophilic by the presence of (i) a topical hydrophilic surfactant thereon, (ii) a hydrophilic melt additive, or both (i) and (ii), wherein the absorbent nonwoven is a hydroentangled spunbond web that has been subjected to a first hydroentanglement process and a second hydroentanglement process, the hydroentangled spunbond web having an outermost surface defined by a three-dimensional pattern formed by the plurality of synthetic fibers, wherein the three-dimensional pattern formed by the plurality of synthetic fibers defines a first outermost surface of the two-layered composite; and
    (b) a second layer that is a liquid-impermeable film, wherein the liquid-impermeable film is an extrusion coated film located directly onto and impregnating at least a plurality of voids between individual spubonbond fibers of the hydroentangled spunbond web to provide an extrusion coated film at least partially embedded into the hydroentangled spunbond web; and wherein the composite a normalized absorbency (g/g) from 10 to 20 and has a lint level of at most about 2000 particles/cubic foot as determined according to test method IS09073-10:2003 and wherein the composite has a Spill Absorption Time of less than 20 seconds and a Spread Index from 1 to 35 cm, and wherein the synthetic fibers are selected from the group consisting of a polyolefin, a polyester, a polyamide, and any combinations thereof.

2. The composite according to claim 1, wherein the liquid-impermeable film is extrusion coated on the absorbent nonwoven.

3. The composite according to claim 1, wherein the absorbent nonwoven comprises bicomponent fibers having a sheath and a core; wherein the sheath comprises a first polyolefin and the core comprises a second polyolefin or a polyester.

4. The composite according to claim 1, wherein the composite has a normalized absorbency from about 5 to about 20.

5. The composite according to claim 1, wherein the composite has a 1 mL Absorption Time of less than 10 seconds.

6. The composite according to claim 1, wherein the composite has a Spread Index from about 1 to about 35.

7. The composite according to claim 1, wherein the first hydroentanglement process is performed on a flat belt.

8. The composite according to claim 7, wherein the second hydroentanglement process is performed on an image transfer sleeve.

9. The composite according to claim 7, wherein the second hydroentanglement process comprises a fluid pressure from 1400 to 3500 psi.

10. A three-layered composite, comprising:
(a) a first layer that is an absorbent nonwoven consisting of a plurality of synthetic fibers rendered hydrophilic by the presence of (i) a topical hydrophilic surfactant thereon, (ii) a hydrophilic melt additive, or both (i) and (ii), and wherein the absorbent nonwoven is a hydroentangled spunbond web that has been subjected to a first hydroentanglement process and a second hydroentanglement process;
(b) a second layer that is a liquid-impermeable film, wherein the liquid-impermeable film comprises a breathable film that is impermeable to liquid water and permeable to water vapor; wherein the breathable film is at least partially embedded into the hydroentangled spunbond web; and
(c) a third layer that is a second nonwoven that is a non-absorbent nonwoven, wherein the liquid-impermeable film is extrusion coated directly between the absorbent nonwoven and the non-absorbent nonwoven, wherein the composite has a Spill Absorption Time of less than 20 seconds and a Spread Index from 1 to 35 cm.

11. The composite of claim 10, wherein the plurality of synthetic fibers are selected from the group consisting of a polyolefin, a polyester, a polyamide, and any combinations thereof.

12. A composite of claim 11, wherein the liquid-impermeable film is extrusion coated on the absorbent nonwoven.

13. A two-layered composite, consisting of:
(a) a first layer that is an absorbent nonwoven consisting of a plurality of synthetic fibers rendered hydrophilic by the presence of a topical hydrophilic additive, and an antimicrobial additive, wherein the absorbent nonwoven is a hydroentangled spunbond web that has been subjected to a first hydroentanglement process and a second hydroentanglement process, the hydroentangled spunbond web having an outermost surface defined by a three-dimensional pattern formed by the plurality of synthetic fibers, wherein the three-dimensional pattern formed by the plurality of synthetic fibers defines a first outermost surface of the two-layered composite; and
(b) a second layer that is a liquid-impermeable film, wherein the liquid-impermeable film is extrusion coated directly onto and is at least partially embedded into the absorbent nonwoven;
wherein the plurality of synthetic fibers are selected from the group consisting of a polyolefin, a polyester, a polyamide, and any combinations thereof.

* * * * *

UNITED STATES PATENT AND TRADEMARK OFFICE
CERTIFICATE OF CORRECTION

PATENT NO. : 12,226,181 B2
APPLICATION NO. : 15/000750
DATED : February 18, 2025
INVENTOR(S) : Lei Wang et al.

It is certified that error appears in the above-identified patent and that said Letters Patent is hereby corrected as shown below:

In the Claims

In Column 24, Claim 1, Line 32, "individual spubonbond" should read as -- individual spunbond --

Signed and Sealed this
Tenth Day of June, 2025

Coke Morgan Stewart
*Acting Director of the United States Patent and Trademark Office*